United States Patent [19]

Claren et al.

[11] Patent Number: 4,535,635
[45] Date of Patent: Aug. 20, 1985

[54] PRESSURE MEASURING SYSTEM

[75] Inventors: Jan S. Claren, Lund; Jan-Bertil Jeppsson, Lomma; Peter R. Staehr, Lund, all of Sweden

[73] Assignee: Gambro Lundia AB, Sweden

[21] Appl. No.: 622,798

[22] Filed: Jun. 21, 1984

[30] Foreign Application Priority Data

Jun. 30, 1983 [SE] Sweden ................................ 8303740

[51] Int. Cl.³ .............................................. G01L 7/08
[52] U.S. Cl. ....................................... 73/756; 73/726; 73/730
[58] Field of Search ................... 73/756, 730, 726, 727

[56] References Cited
U.S. PATENT DOCUMENTS
4,227,420 10/1980 Lamadrid .............................. 73/756

Primary Examiner—Donald O. Woodiel
Attorney, Agent, or Firm—Lerner, David, Littenberg, Krumholz & Mentlik

[57] ABSTRACT

An apparatus is disclosed for measuring the pressure of a fluid comprising a pressure sensing element and a pressure transmitting element. The pressure transmitting element has at least one inlet for receiving the fluid whose pressure is to be measured and a pressure transmitting wall member in fluid communication with the inlet, whereby the pressure transmitting wall member may be brought into contact with the pressure sensing element and a source of vacuum for drawing the pressure transmitting wall member against the pressure sensing element so that the pressure sensing element can substantially measure the absolute pressure of the fluid.

20 Claims, 8 Drawing Figures

PRESSURE MEASURING SYSTEM

FIELD OF THE INVENTION

The present invention relates to a system for measuring the pressure of a fluid, and more particularly, the present invention relates to a system for measuring the pressure of a fluid in connection with the extracorporeal treatment of blood.

BACKGROUND OF THE INVENTION

It is known that during the extracorporeal treatment of blood, it is necessary to measure the pressure of either the blood or some other fluid included in the treatment. Normally, the fluid, such as blood, whose pressure is to be measured is connected up directly or via a filter to a pressure gauge wherein a positive, as well as negative, pressure can be measured. However, with such systems it has been found that coupling problems arise, since the elements carrying the fluid to be measured—for example, a flexible blood tube—are intended to be used only once, whereas the pressure gauge is intended to be used numerous times. Accordingly, problems arise with contamination and sterilization of the pressure gauge.

There is disclosed in U.S. Pat. No. 4,194,974 a system for measuring pressure which attempts to alleviate these coupling problems by allowing the pressure to be transferred mechanically from an elastic pressure pad to a pressure gauge. However, it has been found that the utilization of this system is not suitable for the measurement of negative pressures but, rather, is primarily used for checking that a maximum negative and/or positive pressure are not exceeded.

Another generally known method for measuring a negative pressure consists of comparing the negative pressure with a referenced pressure so as to arrive at a positive pressure difference which can be measured by any suitable method. This also has been found to be nonacceptable, since this procedure becomes relatively complicated because the absolute pressure is not measured directly.

SUMMARY OF THE INVENTION

In accordance with the present invention, it has been discovered that these disadvantages can be overcome by an apparatus for measuring the pressure of a fluid comprising pressure sensing means and pressure transmitting means, the pressure transmitting means having at least one inlet for receiving the fluid whose pressure is to be measured, and a pressure transmitting wall member in fluid communication with the inlet, whereby the pressure transmitting wall member may be brought into contact with the pressure sensing means, and negative pressure means for drawing the pressure transmitting wall member against the pressure sensing means so that the pressure sensing means can substantially measure the absolute pressure of the fluid.

More particularly, the present invention relates to an apparatus of the above-mentioned type characterized in that the pressure transmitting means include an outlet in fluid communication with the inlet, whereby the pressure of the fluid may be measured as the fluid is flowing between the inlet and the outlet.

In accordance with one embodiment of the apparatus of the present invention for the measuring of the pressure of a fluid, including support means, and support means including a receptacle adapted to the pressure transmitting means, the pressure sensing means being mounted on the support means in contact with the receptacle whereby the pressure transmitting means is received in the receptacle, the pressure transmitting wall member of the pressure transmitting means is brought into contact with the pressure sensing means.

In accordance with an embodiment of the apparatus of the present invention, the receptacle includes sealing means whereby the pressure transmitting wall member and the pressure sensing means may be sealed with respect to atmospheric pressure when the pressure transmitting means is received by the receptacle.

In accordance with the preferred embodiment of the apparatus for the measuring of the pressure of a fluid, the pressure transmitting means comprises a generally cylindrical container having a base comprising the pressure transmitting wall member, a side wall substantially perpendicular to the base, and an upper wall portion defining a fluid cavity between the upper wall and the base.

In accordance with the preferred embodiment discussed above, the sealing means comprises a protective sleeve insertable within the receptacle, whereby the protective sleeve can be positioned between the pressure sensing means and the pressure transmitting means.

In accordance with one embodiment of the apparatus of the present invention, the protective sleeve includes sealing elements for sealing the pressure sensing means and pressure transmitting means from atmospheric pressure.

In accordance with another embodiment of the present invention, the sealing elements comprise intricately molded rings on the protective sleeve.

In accordance with another embodiment of the apparatus of the present invention, the protective sleeve includes a base portion adapted to be juxtaposed with the pressure sensing means when the pressure transmitting means is received in the receptacle, the base portion including perforations therein whereby the negative pressure means can operate directly on the pressure transmitting wall member through the perforations.

In accordance with the preferred embodiment of the apparatus of the present invention, the pressure transmitting means and the protective sleeve are formed from thin elastic material and are disposable.

BRIEF DESCRIPTION OF THE DRAWINGS

The invention will be described in further detail with reference to the attached drawings, which show the use of a preferred embodiment of the invention and which.

DETAILED DESCRIPTION OF THE INVENTION

Figure 1:
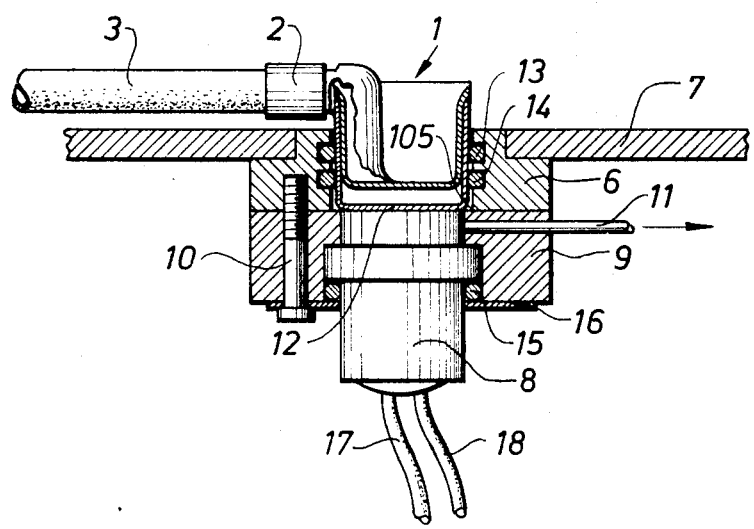
FIG. 1 is an elevational partially cutaway view of the system for measuring pressure of the present invention.
Figure 2:
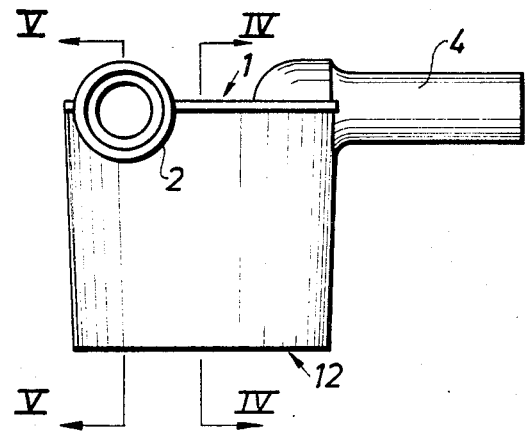
FIG. 2 is an elevational view of the container of the present invention.
Figure 3:
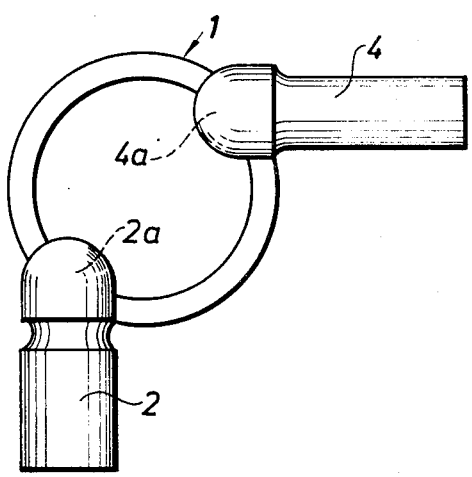
FIG. 3 is a top elevational view of the container of the present invention.
Figure 4:
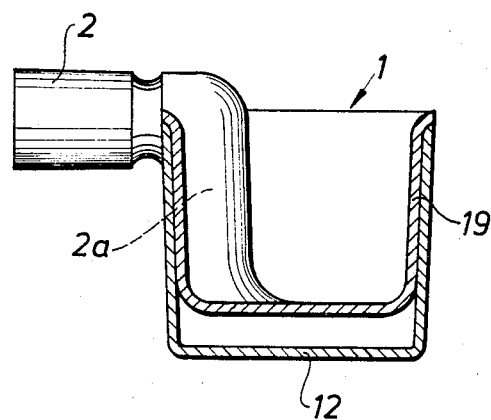
FIG. 4 is a cross-sectional view of the container of the present invention taken along the lines IV—IV in FIG. 2.
Figure 5:
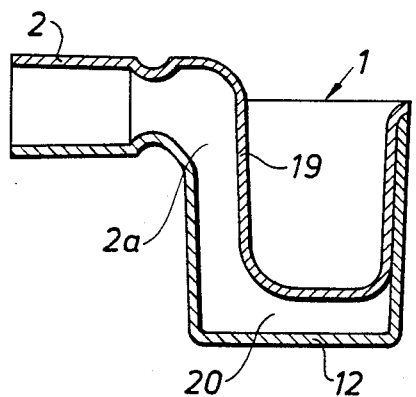
FIG. 5 is a cross-sectional view of the container of the present invention taken on the lines V—V in FIG. 2.

The present invention will be discussed in more detail with reference to FIGS. 1-5, wherein there is shown a pressure transmitting means or container 1 being of generally cylindrical shape having side wall 1a, inlet 2, outlet 4, and a pressure transmitting wall member 12 at the base of side wall 1a. Container 1 can be readily included as a natural component in a flexible tube system which is normally used, for example, with hemodialysis, PD hemofiltration, or plasmaphoresis, whereby a flexible tube 3 carrying the fluid can be coupled to inlet 2 and outlet 4, allowing the fluid to enter and exit container 1.

Container 1 is further comprised of a sunken or indented upper wall 19 which is contiguous with inlet 2 and outlet 4. Upper wall 19 cooperates with side wall 1a and pressure transmitting wall member 12 to form duct 2a, chamber 20, and duct 4a, thereby cooperating to provide a fluid passageway in container 1. Accordingly, the volume of the passageway cooperatively formed by duct 2a, chamber 20, and duct 4a is much less than that of the entire volume of container 1. This is important when the fluid is blood, since it requires the smallest possible volume. Therefore, the "priming" volume or measuring volume of the fluid can be kept relatively low.

In operation a fluid is passed into inlet 2 through flexible tube 3, flowing downwardly through duct 2a to chamber 20 where the measurement of the pressure of the fluid is achieved and then passed upwardly through duct 4a to exit through outlet 4 into a flexible tube (not shown).

Container 1 can be formed by blow molding, or alternatively, it may be produced by injection molding into a shape that can be adapted to the present system. Container 1 is formed of a material that allows a user of the system to dispose of the container after each application. Further, since pressure transmitting wall member 12 must be elastic or yielding such that it does not substantially affect the measurement of the absolute measure in container 1, pressure transmitting wall member 12 may be molded in one piece with container 1 or may be a diaphragm, clamped or welded to container 1.

Referring once again to FIG. 1, there is shown a monitor 6 having a front plate 7. Monitor 6 is utilized as a control for hemodialysis, PD hemofiltration, or plasmaphoresis. Monitor 6 is provided with a receptacle or cavity 5 adapted to receive therein container 1. Mounted on monitor 6 is pressure sensing means 8 having a pressure monitoring surface 8a wherein pressure monitoring surface 8a is positioned in monitor 6 to contact pressure transmitting wall member 12 of container 1 when container 1 is inserted into cavity 5. Pressure sensing means 8 may be a piezoelectric pressure pickup or alternatively may be a wire strain pickup or some other suitable pressure measuring element. Pressure sensing means 8 is rigidly mounted to monitor 6 by machine component 9 which can be screwably adaptable to monitor 6 or may be affixed to monitor 6 through the use of lockwasher 16 and bolt 10.

Machine component 9 is provided with duct 11, which is in communication with a source of vacuum (not shown). In operation, a vacuum is created such that when container 1 is inserted into cavity 5, pressure transmitting wall member 12 of container 1 is fastened by suction onto pressure monitoring surface 8a of pressure sensing means 8. Accordingly, by contacting pressure transmitting wall member 12 of container 1 with pressure monitoring surface 8a through the use of a negative pressure, the pressure monitoring surface 8a can then measure the absolute pressure of the fluid contained in chamber 20 of container 1 by sensing the deflection of pressure transmitting wall member 12. To transmit the measurement of absolute pressure sensed by pressure monitoring surface 8a to a pressure gauge or the like, pressure sensing means 8 is provided with electrical connections 17 and 18, respectively.

To achieve the necessary vacuum, pressure transmitting wall member 12 and pressure monitoring surface 8a of pressure sensing means 8 are sealed against the surrounding atmosphere through the use of annular seals 13, 14, and 15, respectively. Annular seals 13, 14, and 15 can be O-rings or any other suitable seal.

Since container 1 is a plastic component not rigidly affixed to monitor 6 or pressure sensing means 8 but, rather, held in cavity 5 through the use of a negative pressure, it is readily apparent that container 1 is easily removable from monitor 6. Further, since the fluid flowing through container 1 never contacts pressure sensing means 8, the problem of contamination of pressure sensing means 8 is never a problem. Accordingly, the present invention provides for the disposability and therefore replaceability of container 1 without the need for replacing or decontaminating of pressure sensing means 8.

Figure 6:
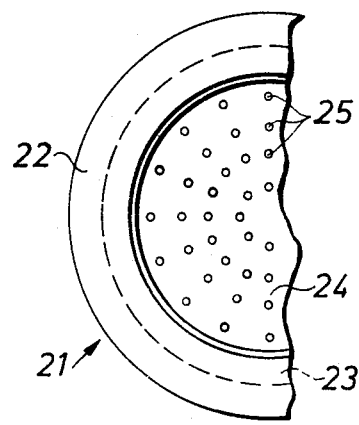
FIG. 6 is a fragmentary top view of a protective sleeve which may form a part of the system in accordance with the present invention.

In an alternative embodiment, as shown in FIG. 6, sealing rings 13 and 14 can be replaced by a thin elastic protective sleeve 21. Protective sleeve 21 generally conforms to the shape of cavity 5 and is positioned within cavity 5 prior to the introduction of container 1. Protective sleeve 21 is comprised of bottom wall 24, side wall 26, one or more annular flanges 23 integrally molded therein, and a lip seal 22 which rests on front plate 7 of monitor 6. To allow tight fastening of container 1 in cavity 5 due to the negative pressure generated by the vacuum, bottom wall 24 of protective sleeve 21 is provided with perforations 25. The purpose of protective sleeve 21 is to prevent and therefore protect pressure sensing means 8 against any leakage arising in the system. As with container 1, if protective sleeve 21 becomes contaminated, it is disposable and can easily be replaced. As previously stated, protective sleeve 21 is formed of a thin elastic material such that it will not affect the measurement of the pressure of the fluid passing through container 1 by retarding the deflection of pressure transmitting wall member 12.

Figure 7:
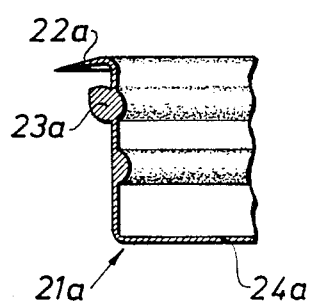
FIG. 7 is a cross-sectional view of one embodiment of the protective sleeve shown in FIG. 6.

Referring now to FIG. 7, there is shown one embodiment of protective sleeve 21, indicated as 21a. Protective sleeve 21a is provided with a lip seal 22a, which when inserted into cavity 5 rests against machine front 7. Protective sleeve 21a is also provided with integrally molded annular solid flanges 23a which cooperatively together with lip flange 21a replace sealing rings 13 and 14 as shown in FIG. 1 to preserve the vacuum condition of the system. Protective sleeve 21a is also provided with a bottom wall 24a, bottom wall 24a also being provided with perforations 25.

Figure 8:
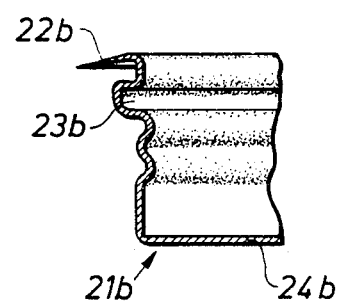
FIG. 8 is a cross-sectional view of another embodiment of the protective sleeve shown in FIG. 6.

As shown in FIG. 8, a second embodiment of protective sleeve 21 is shown whereby protective sleeve 21b also is comprised of a lip member 22b, bottom wall member 24b having perforations 25, and rather than solid annular flanges 23a as shown in FIG. 7, protective sleeve 21b is provided with integrally molded hollow annular flanges 23b.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What we claim is:

1. Apparatus for measuring the pressure of a fluid comprising pressure sensing means and pressure transmitting means, said pressure transmitting means having at least one inlet for receiving said fluid whose pressure is to be measured and a pressure transmitting wall member in fluid communication with said inlet, whereby said pressure transmitting wall member may be brought into contact with said pressure sensing means, and negative pressure means for drawing said pressure transmitting wall member against said pressure sensing means so that said pressure sensing means can substantially measure the absolute pressure of said fluid.

2. The apparatus of claim 1 wherein said pressure transmitting means includes an outlet in fluid communication with said inlet, whereby said pressure of said fluid may be measured as said fluid is flowing between said inlet and said outlet.

3. The apparatus of claim 1 or 2 including support means, and support means including a receptacle adapted to said pressure transmitting means, said pressure sensing means being mounted on said support means in contact with said receptacle whereby when said pressure transmitting means is received in said receptacle, said pressure transmitting wall member of said pressure transmitting means is brought into contact with said pressure sensing means.

4. The apparatus of claim 3 wherein said receptacle includes sealing means whereby said pressure transmitting wall member and said pressure sensing means may be sealed with respect to atmospheric pressure when said pressure transmitting means is received by said receptacle.

5. The apparatus of claim 4 wherein said sealing means comprise O-rings.

6. The apparatus of claim 4 wherein said sealing means comprises a protective sleeve insertable within said receptacle, whereby said protective sleeve can be positioned between said pressure sensing means and said pressure transmitting means.

7. The apparatus of claim 6 wherein said protective sleeve includes sealing elements for sealing said pressure sensing means and pressure transmitting means from atmospheric pressure.

8. The apparatus of claim 7 wherein said sealing elements comprise integrally molded rings on said protective sleeve.

9. The apparatus of claim 8 wherein said protective sleeve includes a base portion adapted to be juxtaposed with said pressure sensing means when said pressure transmitting means is received in said receptacle, said base portion including perforations therein, whereby said negative pressure means can operate directly on said pressure transmitting wall member through said perforations.

10. The apparatus of claim 6 wherein said protective sleeve is formed of a thin elastic material.

11. The apparatus of claim 3 wherein said pressure transmitting means and said receptacle have substantially identical shapes.

12. The apparatus of claim 11 wherein said fluid cavity comprises only a small portion of the volume of said container.

13. The apparatus of claim 1 wherein said pressure sensing means comprises a wire-strain pickup.

14. The apparatus of claim 1 wherein said pressure sensing means comprises a piezoelectric pressure pickup.

15. The apparatus of claim 1 wherein said pressure transmitting means is disposable.

16. The apparatus of claim 1 wherein said fluid comprises fluid being subjected to extracorporeal treatment.

17. The apparatus of claim 1 wherein said pressure transmitting means comprises a generally cylindrical container having a base comprising said pressure transmitting wall member, a side wall substantially perpendicular to said base, and an upper wall portion defining a fluid cavity between said upper wall and said base.

18. The apparatus claim 17 wherein said pressure transmitting wall member is elastic.

19. The apparatus of claim 18 wherein said pressure transmitting wall member is molded integrally with said container.

20. The apparatus of claim 17 wherein said pressure transmitting wall member comprises a diaphragm affixed to said container.

* * * * *